US008492598B2

(12) United States Patent
Harrod et al.

(10) Patent No.: US 8,492,598 B2
(45) Date of Patent: Jul. 23, 2013

(54) METHODS OF REMOVING IMPURITIES FROM ALKYL BROMIDES DURING DISTILLATION AND DISTILLATE PRODUCED THEREIN

(75) Inventors: William B. Harrod, Minden, LA (US); Dru J. Manuel, Magnolia, AR (US); Keith G. Anderson, Baton Rouge, LA (US); Aaron C. Williams, Taylor, AR (US); Kimberly A. Maxwell, Baton Rouge, LA (US)

(73) Assignee: Albemarle Corporation, Baton Rouge, LA (US)

( * ) Notice: Subject to any disclaimer, the term of this patent is extended or adjusted under 35 U.S.C. 154(b) by 626 days.

(21) Appl. No.: 12/674,257

(22) PCT Filed: Aug. 28, 2008

(86) PCT No.: PCT/US2008/074640
§ 371 (c)(1),
(2), (4) Date: Feb. 19, 2010

(87) PCT Pub. No.: WO2009/042344
PCT Pub. Date: Apr. 2, 2009

(65) Prior Publication Data
US 2011/0112342 A1 May 12, 2011

Related U.S. Application Data

(60) Provisional application No. 60/975,053, filed on Sep. 25, 2007.

(51) Int. Cl.
*C07C 17/38* (2006.01)

(52) U.S. Cl.
USPC .......................................................... 570/262

(58) Field of Classification Search
None
See application file for complete search history.

(56) References Cited

U.S. PATENT DOCUMENTS 3,303,107 A 2/1967 Locke
3,876,509 A 4/1975 Davis et al.

FOREIGN PATENT DOCUMENTS

| EP | 0 609 004 | | 8/1994 |
| EP | 609004 A1 | * | 8/1994 |
| EP | 994929 B1 | * | 9/2004 |
| WO | WO 2006/113307 | | 10/2006 |
| WO | WO 2006113307 A1 | * | 10/2006 |
| WO | WO 2006/119212 | | 11/2006 |

* cited by examiner

*Primary Examiner* — Johann R Richter
*Assistant Examiner* — Medhanit Bahta
(74) *Attorney, Agent, or Firm* — Marcy M. Hoefling; Jeremy J. Kliebert; James A. Jubinsky

(57) ABSTRACT

Methods are provided for removing impurities from compositions comprising alkyl bromide. Such methods comprise combining such composition with at least one nonvolatile epoxide during distillation to purify the alkyl bromide. Ultra pure alkyl bromide compositions are also provided.

10 Claims, 2 Drawing Sheets

Figure 1:
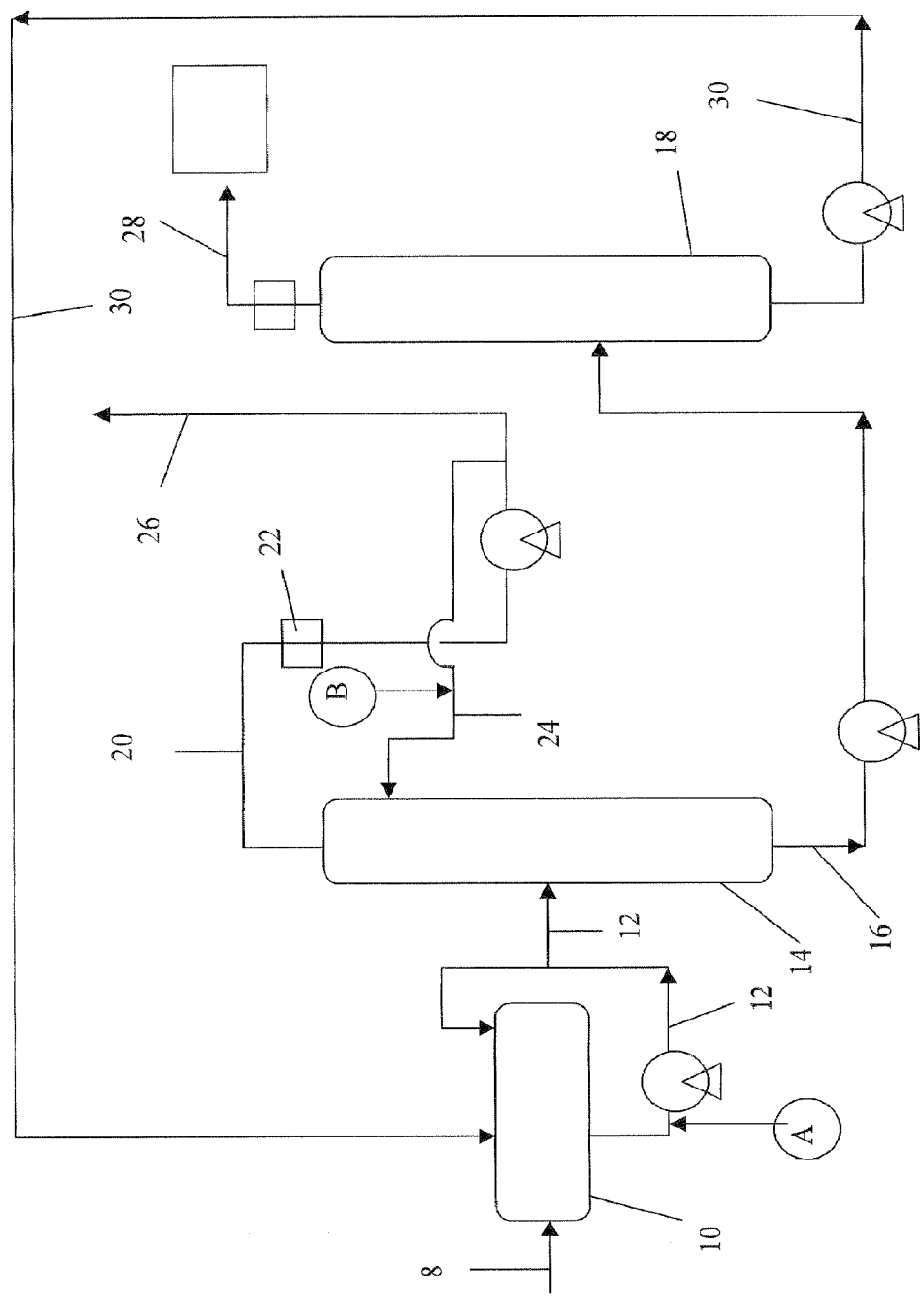

METHODS OF REMOVING IMPURITIES FROM ALKYL BROMIDES DURING DISTILLATION AND DISTILLATE PRODUCED THEREIN

BACKGROUND n-Propyl bromide (also referred to as 1-bromopropane, propyl bromide or NPB) is a commercial product. It is particularly useful as a degreasing agent and is used for various applications including cold cleaning of electrical and mechanical parts.

Methods for producing n-propyl bromide are known. One such method involves free radical hydrobromination of propylene. A variant of this method comprises continuously feeding propylene, gaseous hydrogen bromide, and a molecular oxygen-containing gas into a liquid phase reaction medium comprised of aliphatic bromide (preferably n-propyl bromide, corresponding to the product being produced) to cause anti-Markovnikov addition of HBr to propylene. The principal product is n-propyl bromide with small amounts of isopropyl bromide (also referred to as 2-bromopropane) also being co-formed. WO 2006/113307 describes a process for oxygen-initiated hydrobromination of propylene to form a crude reaction mixture of n-propyl bromide. These and other methods typically produce n-propyl bromide that includes impurities, such as isopropyl bromide and 1,2-dibromopropane, that are undesirable for most applications.

Conventional distillation procedures can be used to remove impurities and thus purify propyl bromide products formed by the hydrobromination of propylene. However, such distillations typically require expensive distillation facilities operated under close control of conditions if highly pure n-propyl bromide is to be recovered.

Thus, there is a need for improved methods for purification of n-propyl bromide and other alkyl bromides.

THE INVENTION

This invention meets the above-described needs by providing methods of removing impurities from a composition comprising an alkyl bromide, such methods comprising combining the composition with at least one nonvolatile epoxide during distillation of the composition. Also provided are such methods wherein the alkyl bromide is 1-bromopropane (n-propyl bromide), wherein the alkyl bromide is 1-bromopropane (n-propyl bromide) that was derived from propylene, and/or wherein the alkyl bromide is 1-bromopropane that was derived from hydrobromination of propylene. Additionally, such methods are provided wherein the at least one nonvolatile epoxide comprises one or more alkyl epoxide having a chain length ranging from $C_{10}$ to $C_{16}$, wherein the at least one nonvolatile epoxide comprises 1,2-epoxydecane or 1,2-epoxyhexadecane, wherein the at least one nonvolatile epoxide comprises a nonvolatile epoxide containing an aromatic ring, and/or wherein the at least one nonvolatile epoxide comprises bis(4-glycidyloxyphenyl)methane or epoxides derived from bisphenol-A, including all epoxy resins thereof. This invention provides methods of removing impurities from a composition comprising n-propyl bromide, the method comprising combining the composition with at least one nonvolatile epoxide during distillation of the composition. This invention provides methods of removing impurities from a composition comprising 1-bromopropane (n-propyl bromide) that has been derived from hydrobromination of propylene, the method comprising combining the composition with at least one nonvolatile epoxide during distillation of the composition.

Also provided by these inventions are a continuously produced distillate composition comprising 1-bromopropane with a purity of greater than about 99.8%, and such continuously produced distillates which have been derived by combining a composition comprising 1-bromopropane with at least one nonvolatile epoxide during distillation of the composition. Also provided are continuously produced distillate compositions comprising 1-bromopropane having a 2-bromopropane content of less than about 120 ppm (wt/wt), and such continuously produced distillate compositions which have been derived by combining a composition comprising 1-bromopropane with at least one nonvolatile epoxide during distillation of the composition.

Methods of this invention are applicable to removal of impurities from any alkyl bromide composition derived by any method now known or that may be developed for deriving such alkyl bromide composition from an alkene. For the sake of illustration, the following description relates to removing impurities from a propyl bromide composition derived from hydrobromination of propylene. Processes for deriving a composition comprising propyl bromide by hydrobromination of propylene are known in the art. The thus derived composition contains propyl bromide and impurities such as isopropyl bromide, 1,2-dibromopropane, acetone, bromoacetone, n-propyl alcohol and n-propyl ether, and the like.

Figure 2:
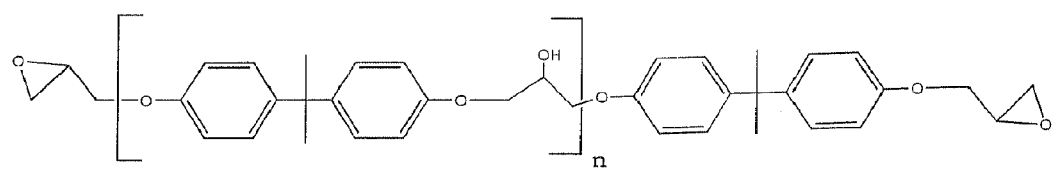

As used in the description of this invention and in the claims, the term "nonvolatile epoxide" means any epoxide that has substantially no evaporation at ambient conditions; examples include bis(4-glycidyloxyphenyl)methane, 1,2-epoxydecane, 1,2-epoxyhexadecane, and certain Dow aromatic epoxy resins such as those having the structure shown in FIG. 2, in which n can be from about 0 to about 0.5, e.g., n can be 0.15. It is desirable for n to be as close to zero as possible to minimize cross-linking and polymerization. Other nonlimiting examples include 1,2 epoxy alkanes having the structure:

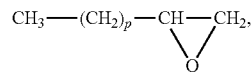

where p is a value in the range of 10-17; e.g., p can be, for example, 10, 12.5, 15.7, etc.

FIGURES

The invention will be better understood by reference to the Figures in which:

FIG. 1 represents a flow diagram of a method conducted according to this invention; and FIG. 2 shows the chemical structure for exemplary nonvolatile epoxides suitable for use in methods of this invention.

DESCRIPTION

An exemplary process for separating NPB from a crude mixture comprising NPB and isopropyl bromide (IPB) can comprise first washing at least a portion of the crude mixture one or more times with a wash comprising an aqueous solution or aqueous suspension of at least one alkali metal hydroxide. After separating the phases by conventional means, at least a portion of the organic phase can optionally be washed with water to form an organic phase and an aqueous phase. Whether or not the optional water wash is performed, the phases can be separated and one or more distillations carried out on at least a portion of the organic phase so separated, to form a highly pure propyl bromide product.

Distillation conditions are desirably established to inhibit isopropyl bromide formation (due to isomerization) in the columns. Desirably, isopropyl bromide concentrations, even absent addition of nonvolatile epoxides according to this invention, would be between about 75 ppm wt and about 300 ppm due to the distillation conditions. However, alkyl bromide compositions purified according to methods of this invention can have an isopropyl bromide concentrations lower than about 100 ppm wt, e.g., lower than about 50 ppm wt.

According to this invention, at least one nonvolatile epoxide is combined with a composition comprising an alkyl bromide during distillation of the composition. Suitable amounts of nonvolatile epoxides can be combined with the composition. For example, without thereby limiting this invention, 100-300 ppm of nonvolatile epoxides in the composition once combined can be suitable in a dry crude storage tank prior to entry into distillation columns, and 150-300 ppm of nonvolatile epoxides in the composition once combined can be suitable as feed to, or inside, the distillation column(s).

Methods of this invention can be better understood by referring to FIG. 1, which illustrates a continuous distillation process in accordance with this invention. For example, feed 1-bromopropane can be pumped from container 10 via conduit 12 to distillation column 14. Feed 1-bromopropane in container 10 can originate from any suitable source, as will be familiar to those skilled in the art, and fed into container 10, e.g., via conduit 8. Purified crude product can exit distillation column 14 during distillation within column 14, via conduit 16 and be pumped into distillation column 18. An overhead stream can exit distillation column 14 via conduit 20, be cooled in condenser 22, and thereafter at least a portion can be pumped back into distillation column 14 as reflux via conduit 24 and at least a portion can be removed from the distillation process as impurities via conduit 26. The purified crude product that is pumped into distillation column 18 can be further distilled within column 18. Product purified 1-bromopropane can exit column 18 via conduit 28; and bottoms can exit column 18 via conduit 30 and recycled back to container 10. In accordance with this invention, one or more nonvolatile epoxides can be added to feed 1-bromopropane in conduit 12, e.g., at site A, and/or to reflux in conduit 24, e.g., at site B, via means known to those skilled in the art, and thus improve the purity of product purified 1-bromopropane in conduit 28. Additionally, residual nonvolatile epoxides in bottoms in conduit 30 recycled to container 10 for combining with feed 1-bromopropane also assists in improving purity of product 1-bromopropane. Distillations conducted in columns 14 and 18 can be conducted under appropriate conditions, as are familiar to those skilled in the art.

Methods of this invention can be applied to distillation of alkyl bromides produced from alcohols. The nonvolatile epoxide can be added at a point beyond the removal of the alcohol to minimize formation of ether linkages. Thus, it is especially useful in the secondary distillation steps if the alcohol is removed either by washing or an initial distillation followed by additional distillation.

This invention is particularly advantageous in that HBr produced from dehydrobromination, and/or from reaction of reactive organics such as bromoacetone in the system, is scavenged by the nonvolatile epoxide. This has the additional effect of minimizing the traces of bromine in the system and therefore minimizes the amount of dehydrobromination catalyst ($FeBr_3$) that is made. For example, 1 mole of HBr can react with one mole of epoxy functional group to produce a bromohydrin. Bromohydrins, in turn, can be oxidized by traces of halogen to form alpha bromoketones. Oxidation of elemental iron is minimized, which has the potential benefit of decreasing corrosion of the distillation columns, thus minimizing plant downtime while spare parts are ordered.

EXAMPLES

The following examples are illustrative of the principles of this invention. It is understood that this invention is not limited to any one specific embodiment exemplified herein, whether in the examples or the remainder of this patent application.

Examples

Analytical Method

Gas chromatography (GC) analyses were performed using an Agilent Technologies Model 6890N Series GC with a flame ionization detector and He carrier gas with a split injector and 9.4 psig column head pressure and He flow velocity 33 mL/min, using a 30 m×0.32 mm DB-624 column with a film thickness of 1.8 um. GC thermal conditions were as follows: Injector 150° C., detector 250° C., Oven initial: 40° C., held 8 minutes, increased at a rate of 5C.°/min to 70° C. then increased 15C.°/min to a final temperature of 250° C., then held at final temperature for 5 minutes. Samples analyzed (1 uL) without dilution in order to quantify the impurities, particularly 2-bromopropane, down to concentrations of <25 ppm wt.

Four nonvolatile epoxide additives (1,2-epoxydecane, 1,2-epoxyhexadecane, the Dow aromatic epoxy resins having the structure shown in FIG. 2, and bis(4-glycidyloxyphenyl)methane) were tested for potential for surface stabilization and to minimize solution acidity and corrosion in propyl bromide distillation columns. The Dow aromatic epoxy resins comprise the (non-catalyst-containing) resin from the reaction of epichlorohydrin with bisphenol-A. These were spiked to concentrations of 4000-6000 ppm into propyl bromide solutions containing $FeBr_3$ (590-1026 ppm wt), fourteen samples in all. The tests were conducted as thermal stability tests for three days at 50° C. Baseline showed acidity increasing to 154 ppm HBr and 124 ppm Fe for isopropyl bromide substrate solutions. The initial values were 5 ppm HBr and <0.1 ppm Fe at the beginning of the test. 1,2-Epoxydecane had 12 ppm HBr and 7 ppm Fe in solution. Significantly lower solution acidity (1-3 ppm) and very low solution iron content (0.6-2 ppm) was seen for the aromatic epoxides, potentially due to formation of phenoxy-iron complexes.

Example 1

Propyl bromide (137.09 g 1.12 moles) was added along with $FeBr_3$ (0.12 g 0.4 mmoles, 865 ppm wt) and the epoxy resin sold under the Dow tradename DER 383 (1.46 g 1.05% wt) into a 4 oz glass container, sealed with a teflon lid, and stored for three days at 50° C. Analysis by GC indicated the following initial n-propyl bromide composition: 1-bromopropane (99.92%), 2-bromo-propane (34 ppm). The acidity of the initial solution (1 ppm wt, as HBr), was measured by extraction and titration with 0.005N KOH in methanol using bromothymol blue indicator. Upon storage for three days at 50° C., the sample was re-examined and by GC the composition was 1-bromopropane (99.93%), 2-bromopropane (93 ppm) and the HBr concentration was 2 ppm wt.

Example 2

Propyl bromide (127.15 g 1.03 moles) was added along with FeBr$_3$ (0.10 g 0.3 mmoles, 782 ppm wt) and bis(4-glycidyloxyphenyl)methane (0.52 g 1.7 mmoles, 4070 ppm) into a 4 oz glass container, sealed with a teflon lid, and stored for three days at 50° C. Analysis by GC of the initial n-propyl bromide: 1-bromopropane (99.92%), 2-bromopropane (34 ppm). The acidity of the initial propyl bromide was 1 ppm wt (HBr) measured as described in Example 2 above. Upon storage for three days at 50° C., the sample was re-examined and by GC the composition was 1-bromopropane (99.94%), 2-bromopropane (112 ppm), with an HBr concentration of 1 ppm.

Example 3

A Mixture (I) comprised of 523.50 g 2-bromopropane and 581.42 g 1-bromopropane was premixed. A sample (137.51 g) of Mixture (I) was added along with FeBr$_3$ (0.12 g 0.4 mmoles, 866 ppm wt) along with DER 383 (0.94 g 6783 ppm) into a 4 oz glass container, sealed with a teflon lid, and stored for three days at 50° C. GC analysis of the initial mixture of propyl bromide isomers gave: 1-bromopropane (53.13%), 2-bromopropane (46.72%). The acidity of the initial Mixture (I) was 4 ppm wt (HBr), measured as described in Example 2 above. Upon storage for three days at 50° C., the sample was re-examined and by GC the composition was 1-bromopropane (53.17%), 2-bromopropane (46.68%), with an HBr concentration of 3 ppm wt.

Example 4

A sample (136.50 g) of Mixture (I) was added along with FeBr3 (0.09 g 0.3 mmoles, 655 ppm wt) along with bis(4-glycidyloxyphenyl)methane (0.82 g 2.6 mmoles, 5968 ppm) into a 4 oz glass container, sealed with a teflon lid, and stored for three days at 50° C. GC analysis of the initial mixture of propyl bromide isomers gave: 1-bromopropane (53.13%), 2-bromopropane (46.72%). The acidity of the initial Mixture (I) was 4 ppm wt, (HBr), measured as described in Example 2 above. Upon storage for three days at 50° C., the sample was re-examined and by GC the composition was 1-bromopropane (53.21%), 2-bromopropane (46.65%), with an HBr concentration of 2 ppm wt.

Example 5

Comparative Example

Storage Stability of 1-Bromopropane in the Absence of FeBr$_3$

Propyl bromide (132.82 g 1.08 moles) was added into a 4 oz glass container, sealed with a teflon lid, and stored for three days at 50° C. Analysis by GC indicated the following initial composition: 1-bromopropane (99.92%), 2-bromopropane (34 ppm). The acidity of the initial solution (1 ppm wt, as HBr) was measured by extraction and titration with 0.005N KOH in methanol using bromothymol blue indicator. Iron in the initial sample was 2.3 ppm as measured by extraction of typically 30 mL of organic solution with an equal volume of 5N HCl and analysis of the aqueous extract by atomic absorption spectroscopy. Upon storage for three days at 50° C., the sample was re-examined and, by GC analysis, the composition was 1-bromopropane (99.92%), 2-bromopropane (67 ppm), and its HBr concentration was 2 ppm wt.

Example 6

Comparative Example

Storage Stability of a Mixture Enriched in 2-Bromopropane in the Absence of FeBr$_3$ A sample (135.32 g) of Mixture (I) was added into a 4 oz glass container, sealed with a teflon lid, and stored for three days at 50° C. Analysis by GC indicated the following initial composition: 1-bromopropane (53.13%), 2-bromopropane (46.72%). The acidity of the initial solution was 4 ppm wt (HBr), measured as described in Example 6 above. Iron in the initial sample was <1 ppm, measured as described in Example 6 above. Upon storage for three days at 50° C., the sample was re-examined and by GC the composition was 1-bromopropane (53.23%), 2-bromopropane (46.61%), and its HBr concentration was 5 ppm wt.

Example 7

Comparative Example

Effect of FeBr$_3$ Upon Storage Stability of 1-Bromopropane

Propyl bromide (135.34 g 1.10 moles) was added along with FeBr$_3$ (0.08 g 0.3 mmoles, 591 ppm wt) into a 4 oz glass container, sealed with a teflon lid, and stored for three days at 50° C. Analysis by GC indicated the following initial purity of n-propyl bromide: 1-bromopropane (99.92%), 2-bromopropane (34 ppm). The acidity of the initial propyl bromide was (1 ppm wt, as HBr), measured as described in Example 6 above. Upon storage for three days at 50° C., the sample was re-examined and by GC the composition was 1-bromopropane (99.94%), 2-bromopropane (83 ppm), and the HBr concentration was 14 ppm wt.

Example 8

Comparative Example

Effect of FeBr$_3$ Upon Storage Stability of a Mixture Enriched in 2-Bromopropane A sample (107.11 g) of Mixture (I) was added along with FeBr$_3$ (0.11 g 0.4 mmoles, 1026 ppm wt) into a 4 oz glass container, sealed with a teflon lid, and stored for three days at 50° C. Analysis of the Mixture (I) by GC indicated the following initial composition: 1-bromopropane (53.13%), 2-bromopropane (46.72%). The acidity of the initial Mixture (I) was 4 ppm wt (HBr), measured as described in Example 6 above. Upon storage for three days at 50° C., the sample was re-examined and by GC the composition was 1-bromopropane (53.31%), 2-bromopropane (46.50%), with an HBr concentration of 154 ppm wt.

It is to be understood that the reactants and components referred to by chemical name or formula anywhere in the specification or claims hereof, whether referred to in the singular or plural, are identified as they exist prior to being combined with or coming into contact with another substance referred to by chemical name or chemical type (e.g., another reactant, a solvent, or etc.). It matters not what chemical changes, transformations and/or reactions, if any, take place in the resulting combination or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a combination to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, combined, blended or mixed with one or more other substances, components and/or ingredients in accordance with the present disclosure. Whatever transformations, if any, which occur in situ as a reaction is conducted is what the claim is intended to cover. Thus the fact that a substance, component or ingredient may have lost its original identity through a chemical reaction or transformation during the course of contacting, combining, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof. As will be familiar to those skilled in the art, the terms "combined", "combining", and the like as used herein mean that the components that are "combined" or that one is "combining" are put into a container with each other. Likewise a "combination" of components means the components having been put together in a container.

While the present invention has been described in terms of one or more preferred embodiments, it is to be understood that other modifications may be made without departing from the scope of the invention, which is set forth in the claims below.

What is claimed is:

1. A method of removing impurities from a composition comprising an alkyl bromide, the method comprising combining the composition with at least one nonvolatile epoxide during distillation of the composition.

2. The method of claim 1 wherein the alkyl bromide is 1-bromopropane (n-propyl bromide).

3. The method of claim 1 wherein the alkyl bromide is 1-bromopropane (n-propyl bromide) that was derived from propylene.

4. The method of claim 1 wherein the alkyl bromide is 1-bromopropane that was derived from hydrobromination of propylene.

5. The method of claim 1 wherein the at least one nonvolatile epoxide comprises one or more alkyl epoxide having a chain length ranging from $C_{10}$ to $C_{16}$.

6. The method of claim 5 wherein the at least one nonvolatile epoxide comprises 1,2-epoxydecane or 1,2-epoxyhexadecane.

7. The method of claim 1 wherein the at least one nonvolatile epoxide comprises a nonvolatile epoxide containing an aromatic ring.

8. The method of claim 7 wherein the at least one nonvolatile epoxide comprises bis(4-glycidyloxyphenyl)methane or epoxides derived from bisphenol-A, including all epoxy resins thereof.

9. A method of removing impurities from a composition comprising n-propyl bromide, the method comprising combining the composition with at least one nonvolatile epoxide during distillation of the composition.

10. A method of removing impurities from a composition comprising 1-bromopropane (n-propyl bromide) that has been derived from hydrobromination of propylene, the method comprising combining the composition with at least one nonvolatile epoxide during distillation of the composition.

* * * * *

UNITED STATES PATENT AND TRADEMARK OFFICE
CERTIFICATE OF CORRECTION

PATENT NO. : 8,492,598 B2  Page 1 of 1
APPLICATION NO. : 12/674257
DATED : July 23, 2013
INVENTOR(S) : Harrod et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 591 days.

Signed and Sealed this
Eighth Day of September, 2015

Michelle K. Lee
*Director of the United States Patent and Trademark Office*